(12) United States Patent
Hunt et al.

(10) Patent No.: US 7,026,167 B2
(45) Date of Patent: Apr. 11, 2006

(54) SYSTEMS AND METHODS FOR THE ANALYSIS OF PROTEIN PHOSPHORYLATION

(75) Inventors: Donald F. Hunt, Charlottesville, VA (US); Forest M. White, Charlottesville, VA (US); Scott Ficarro, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 223 days.

(21) Appl. No.: 10/330,888

(22) Filed: Dec. 26, 2002

(65) Prior Publication Data

US 2003/0224967 A1 Dec. 4, 2003

Related U.S. Application Data

(60) Provisional application No. 60/343,851, filed on Dec. 28, 2001.

(51) Int. Cl.
- *G01N 24/00* (2006.01)
- *G01N 33/483* (2006.01)
- *C07K 1/36* (2006.01)

(52) U.S. Cl. .................. 436/173; 436/56; 436/86; 530/352; 530/340; 530/345; 530/407; 530/355; 530/343; 530/811

(58) Field of Classification Search ................ 436/173, 436/56, 86; 530/343, 345, 344, 407, 355, 530/811, 352, 340
See application file for complete search history.

(56) References Cited

U.S. PATENT DOCUMENTS

| | | |
|---|---|---|
| 6,020,208 A | 2/2000 | Hutchens et al. |
| 6,271,037 B1 | 8/2001 | Chait et al. |
| 6,329,146 B1 | 12/2001 | Crooke et al. |
| 6,818,454 B1 * | 11/2004 | Goshe et al. ............ 436/173 |

OTHER PUBLICATIONS

Weckwerth, W. et al. (Sep. 2000) Comparative quantification and identification of phosphoproteins using stable isotope labeling and liquid chromatography/mass spectrometry. Rapid Commun. Mass. Spectrom. vol. 14, pp. 1677-1681.*

Zhu, Y. et al. (2000) In vivo microdialysis and reverse phase ion pair liquid chromatography/tandem mass spectrometry for the determination and identification of acetylcholine and related compounds in rat brain. Rapid Comm. Mass Spectr. vol. 14, pp. 1695.*

Oda, Y. et al. Enrichment analysis of phosphorylated proteins as a tool for probing the phosphoproteome. Nat. Biotech. 19, 379-382 (Apr. 2001).

Rossomando, A.J. et al. Identification of Tyr-185 as the site of tyrosine autophosphorylation of recombinant mitogen-activated protein kinase p42mapk. PNAS 89, 5779-5783 (Jul. 1992).

Strong et al. Phosphorylation state of the native high-molecular-weight neurofilament subunit protein from cervical spinal cord in sporadic amyotrophic lateral sclerosis. J. Neurochem. 76, 1315-1325 (Mar. 2001).

Zhou, H. et al. A systematic approach to the analysis of protein phosphorylation. Nat. Biotech. 19, 375-378 (Apr. 2001).

Merchant, M. et al., Recent Advancements in Surface-Enhanced Laser Desorption / Ionization—Time of Flight—Mass Spectrometry. *Electrophoresis* 21: 1164-1177, 2000.

Aebersold, R. and Goodlett, D.R., Mass Spectrometry in Proteomics. Chem. Rev. 101(2): 269-95 (2001).

Ahn, N.G. and Resing, K.A., Toward the Phosphoproteome. Nat. Biotechnol. 19(4): 317-8 (2001).

Jason, J.C. and Ryden, L., Protein Purification. Wiley-Liss, Canada, pp377 (1998).

Stern, D.F., Phosphoproteomics, Exp. Mol. Pathol. 70(3): 327-31 (2001).

* cited by examiner

*Primary Examiner*—Jon Weber
*Assistant Examiner*—Samuel Wei Liu
(74) *Attorney, Agent, or Firm*—Rodney L. Sparks

(57) ABSTRACT

The present invention relates to a method of applying mass spectrometry to analyzing peptides or proteins, especially in the proteome setting. More particularly, the invention relates to a mass spectrometry-based method for detection of protein/peptide phosphorylation wherein the side chains of glutamic acid and/or aspartic acid residues of said peptides or proteins are chemically modified as to improve the selectivity/efficiency of identification of the phosphorylated protein/peptide.

18 Claims, 2 Drawing Sheets

SYSTEMS AND METHODS FOR THE ANALYSIS OF PROTEIN PHOSPHORYLATION

REFERENCE TO RELATED APPLICATIONS

Figure 1:
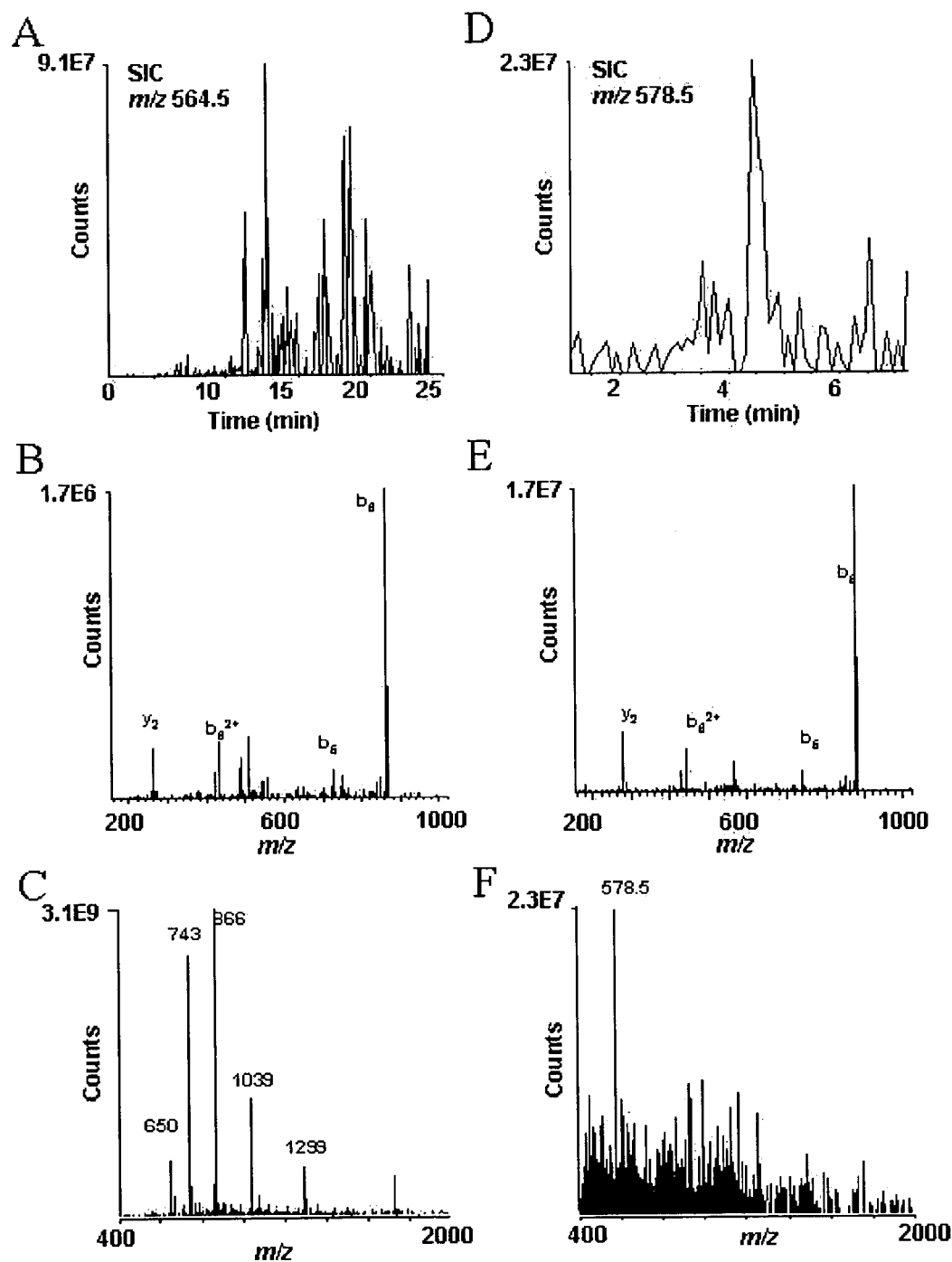

The present application claims priority to U.S. Provisional application No. 60/343,851, filed on Dec. 28, 2001, the entire content of which is incorporated by reference herein.

FIELD OF THE INVENTION

This invention is in the field of proteomics, and applies mass spectrometry to the analysis of peptides and amino acids. More particularly, the invention relates to a mass spectrometry-based method for detection of amino acid phosphorylation.

BACKGROUND TO THE INVENTION

With the availability of a burgeoning sequence databases, genomic applications demand faster and more efficient methods for the global screening of protein expression in cells. However, the complexity of the cellular proteome expands substantially if protein post-translational modifications are also taken into account.

Dynamic post-translational modification of proteins is important for maintaining and regulating protein structure and function. Among the several hundred different types of post-translational modifications characterized to date, protein phosphorylation plays a prominent role. Enzyme-catalyzed phosphorylation and de-phosphorylation of proteins is a key regulatory event in the living cell. Complex biological processes such as cell cycle, cell growth, cell differentiation and cell metabolism are orchestrated and tightly controlled by reversible phosphorylation events which modulate protein activity, stability, interaction and localization. Perturbations in phosphorylation states of proteins, e.g. by mutations which generate constitutively active or inactive protein kinases and phosphatases, play a prominent role in oncogenesis. Comprehensive analysis and identification of phosphoproteins, combined with exact localization of phosphorylation sites in those proteins ('phosphoproteomics') is a prerequisite for understanding complex biological systems and the molecular features leading to disease.

It is estimated that ⅓ of all proteins present in a mammalian cell are phosphorylated and that kinases, enzymes responsible for that phosphorylation, constitute about 1–3% of the expressed genome. Organisms use reversible phosphorylation of proteins to control many cellular processes including signal transduction, gene expression, the cell cycle, cytoskeletal regulation and apoptosis. A phosphate group can modify serine, threonine, tyrosine, histidine, arginine, lysine, cysteine, glutamic acid and aspartic acid residues. However, the phosphorylation of hydroxyl groups at serine (90%), threonine (10%), or tyrosine (0.05%) residues are the most prevalent, and are involved, along with other processes, in metabolism, cell division, cell growth, and cell differentiation. Because of the central role of phosphorylation in the regulation of life, much effort has been focused on the development of methods for characterizing protein phosphorylation.

The identification of phosphorylation sites on a protein is complicated by the facts that proteins are often only partially phosphorylated and that they are often present only at very low levels. Therefore techniques for identifying phosphorylation sites should preferably work in the low picomole to sub-picomole range.

Traditional methods for analyzing O-phosphorylation sites involve incorporation of $^{32}P$ into cellular proteins via treatment with radiolabeled ATP. The radioactive proteins can be detected during subsequent fractionation procedures (e.g. two-dimensional gel electrophoresis or high-performance liquid chromatography [HPLC]). Proteins thus identified can be subjected to complete hydrolysis and the phospho-amino acid content determined. The site(s) of phosphorylation can be determined by proteolytic digestion of the radiolabeled protein, separation and detection of phosphorylated peptides (e.g. by two-dimensional peptide mapping), followed by peptide sequencing by Edman degradation. These techniques can be tedious, require significant quantities of the phosphorylated protein and involve the use of considerable amounts of radioactivity.

In recent years, mass spectrometry (MS) has become an increasingly viable alternative to more traditional methods of phosphorylation analysis. The most widely used method for selectively enriching phosphopeptides from mixtures is immobilized metal affinity chromatography (IMAC). In this technique, metal ions, usually $Fe3+$ or $Ga3+$, are bound to a chelating support. Phosphopeptides are selectively bound because of the affinity of the metal ions for the phosphate moiety. The phosphopeptides can be released using high pH or phosphate buffer, the latter usually requiring a further desalting step before MS analysis. Limitations of this approach include possible loss of phosphopeptides due to their inability to bind to the IMAC column, difficulty in the elution of some multiply-phosphorylated peptides, and background from unphosphorylated peptides (typically acidic in nature) which also have some affinity for immobilized metal ions. Two types of chelating resin are commercially available, one using iminodiacetic acid and the other using nitrilotriacetic acid. Some groups have observed that iminodiacetic acid resin is less specific than nitrilotriacetic acid, whereas another study reported little difference between the two. Several studies have examined off-line MS analysis of IMAC-separated peptides.

Recently, two groups have described protocols to achieve this goal. Oda et al. (*Nat Biotechnol.* 2001 19:379–82) start with a protein mixture in which cysteine reactivity is removed by oxidation with performic acid. Base hydrolysis is used to induce -elimination of phosphate from phosphoserine and phosphothreonine, followed by addition of ethanedithiol to the alkene. The resulting free sulflhydryls are coupled to biotin, allowing purification of phosphoproteins by avidin affinity chromatography. Following elution of phosphoproteins and proteolysis, enrichment of phosphopeptides is carried out by a second round of avidin purification. Disadvantages of this approach include the failure to detect phosphotyrosine containing peptides and the generation of diastereoisomers in the derivatization step.

The approach suggested by Zhou et al. (*Nat Biotechnol* 2001 19:375–378) circumvents these problems but involves a six step derivatization/purification protocol for tryptic peptides which requires more than 13 hrs to complete and affords only a 20% yield from picomoles of phosphopeptide starting material. The method begins with a proteolytic digest which has been reduced and alkylated to eliminate reactivity from cysteine residues. Following N-terminal and C-terminal protection, phosphoramidate adducts at phosphorylated residues are formed by carbodiimide condensation with cystamine. The free sulfhydryl groups produced from this step are covalently captured onto glass beads coupled to iodoacetic acid. Elution with trifluoroacetic acid then regenerates phosphopeptides for analysis by mass spectrometry.

SUMMARY OF THE INVENTION

One aspect of the present invention provides a method for identifying phosphorylated amino acids within a protein by combining affinity purification and mass spectroscopy. In general, the subject method makes use of affinity capture reagents for isolating, from a protein sample, those proteins which have been phosphorylated. In order to improve the selectivity/efficiency of the affinity purification step, the protein samples to be analyzed are chemically modified at one or more of the C-terminal carboxyl or amino acid side chains of the proteins which may interfere with the selectively of the affinity purification step—for example, the side chains of glutamic acid and aspartic acid residues can be converted to neutral derivatives such as by alkyl-esters.

Phosphorylated proteins which are isolated are then analyzed by mass spectroscopy in order to identify patterns of phosphorylation across a proteome, and/or to provide the identity of proteins in the sample which are phosphorylated or to show changes in phosphorylation status between two different samples.

In certain preferred embodiments, the proteins are cleaved into smaller peptide fragments before, after or during the chemical modification step. For instance, the proteins can be fragmented by enzymatic hydrolysis to produce peptide fragments having carboxy-terminal lysine or arginine residues. In certain preferred embodiments, the proteins are fragmented by treatment with trypsin.

In certain embodiments, the proteins are mass-modified with isotopic labels before, after or during the chemical modification step.

In certain embodiments, the proteins are further separated by reverse phase chromatography before analysis by mass spectroscopy.

There are a variety of mass spectroscopy techniques which can be employed in the subject method. In certain preferred embodiments, the isolated proteins are identified from analysis using tandem mass spectroscopy techniques, such as LC/MS/MS (Liquid Chromatography tandem Mass Spectrometry). Where the proteins have been further fragmented with trypsin or other predictable enzymes, the molecular weight of a fragment, as determined from the mass spectroscopy data, can be used to identify possible matches in databases indexed by predicted molecular weights of protein fragments which would result under similar conditions as those generated in the subject method. However, the subject method can also be carried out using mass spectroscopy techniques which produce amino acid sequence mass spectra for the isolated proteins or peptide fragments. The sequence data can be used to search one or more sequence databases.

The subject method is amenable to analysis of multiple different protein samples, particularly in a multiplex fashion. In such embodiments, the proteins or fragments thereof are isotopically labeled in a manner which permits discrimination of mass spectroscopy data between protein samples. That is, mass spectra on the mixture of various protein samples can be deconvoluted to determine the sample origin of each signal observed in the spectra. In certain embodiments, this technique can be used to quantitate differences in phosphorylation levels between samples prepared under different conditions and admixed prior to MS analysis.

In certain embodiments, the subject method is used for analyzing a phosphoproteome. For example, the proteins in the sample can be chemically modified at glutamic acid and aspartic acid residues, such as by alkyl-esterification, to generate neutral side chains at those positions. The phosphorylated proteins in the sample are then isolated by immobilized metal affinity chromatography and analyzed by mass spectroscopy. In preferred embodiments, the proteins are cleaved, e.g., by trypsin digestion or the like, into smaller peptide fragments before, after or during the step of chemically modify the glutamic acid and aspartic acid residues. In one embodiment, the subject method is carried out on multiple different protein samples, and proteins which are differentially phosphorylated between two or more protein samples are identified. That data can, for instance, be used to generate or augment databases with the identity of proteins which are determined to be phosphorylated.

Another aspect of the invention provides a method for identifying a treatment which modulates the phosphorylation of an amino acid in a target polypeptide. In general, this method is carried out by providing a protein sample which has been subjected to a treatment of interest, such as with ectopic agents (drugs, growth factors, etc.). The protein samples can also be derived from normal cells in different states of differentiation or tissue fate, or derived from normal and diseased cells. Following the affinity purification/MS method set forth above, the identity of proteins which have been phosphorylated in the treated protein sample relative to an untreated sample or control sample can determined. From this identification step, one can determine whether the treatment results in a pattern of changes in phosphorylation, relative to the untreated sample or control sample, which meet a pre-selected criteria. Thus, one can use this method to identify compounds likely to mimic the effect of a growth factor by scoring for similarities in phosphorylation patterns when comparing proteins from the compound-treated cells with proteins from the growth factor treated cells. The treatment of interest can include contacting the cell with such compounds as growth factors, cytokines, hormones, or small chemical molecules. In certain embodiments, the method is carried out with various members of a chemically diverse library.

Yet another aspect of the present invention provides a method of conducting a drug discovery business. Using the assay described above, one determines the identity of a compound which produces a pattern of changes in phosphorylation, relative to the untreated sample or control sample, which meet a pre-selected criteria. Therapeutic profiling of the compound identified by the assay, or further analogs thereof, can be carried out to determine efficacy and toxicity in animals. Compounds identified as having an acceptable therapeutic profile can then be formulated as part of a pharmaceutical preparation. In certain embodiments, the method can include the additional step of establishing a distribution system for distributing the pharmaceutical preparation for sale, and may optionally include establishing a sales group for marketing the pharmaceutical preparation. In other embodiments, rather than carry out the profiling and/or formulation steps, one can license, to a third party, the rights for further drug development of compounds which are discovered by the subject assay to alter the level of phosphorylation of the target polypeptide.

Yet another aspect of the present invention provides a method of conducting a drug discovery business in which, after determining the identity of a protein which is phosphorylated under the conditions of interest, the identity of one or more enzymes which catalyze the phosphorylation is determined. Those enzyme(s) are then used as targets in drug screening assays for identifying compounds which inhibit or potentiate the enzymes and which, therefore, can modulate the phosphorylation of the identified protein under the conditions of interest.

REFERENCE TO THE DRAWINGS

FIG. 1. Shows the results obtained from analyses of a phosphopeptide sample by immobilized metal affinity chromatography (IMAC) and nanoflow high-performance liquid chromatography (HPLC) on an liquid chromatography electrospray (LCQ) ion trap mass spectrometer. Five non-phosphorylated proteins; glyceraldehyde 3-phosphate dehydrogenase, bovine serum albumin, carbonic anhydrase, ubiquitin, and β-lactoglobulin (Sigma Chemical Co., St. Louis, Mo.) (100 nmol each) in 1.1 ml of 100 mM ammonium bicarbonate (pH 8) were digested with trypsin (20 μg) (Promega, Madison, Wis.) for 24 h at 37° C. The reaction was quenched with 65 μl of glacial acetic acid, and the mixture diluted to a final volume of 50 ml with 0.1% acetic acid. To this solution was added 500 pmol of HPLC (High Performance Liquid Chromatography) purified phosphopeptide, DRVpYIHPF (SEQ ID NO: 1, Novabiochem, San Diego, Calif.) in 0.1% acetic acid (2 μL of a 250 pmol/μL stock solution). An aliquot of the standard mixture (100 μl) was lyophilized and redissolved in 100 μl of 2 N methanolic HCl. This latter solution was prepared by dropwise addition of 160 μl of acetyl chloride, with stirring, to 1 ml of methanol. Esterification was allowed to proceed for 2 h at room temperature. Solvent was removed by lyophylization and the resulting sample re-dissolved in 100 μl of solution containing equal volumes of methanol, water and acetonitrile. Phosphate methyl esters are not observed under these conditions. Mass spectra recorded by a combination of immobilized metal affinity chromatography (IMAC) and nano-flow HPLC microelectrospray ionization mass spectrometry on the phosphopeptide, DRVpYIHPF (SEQ ID NO: 1), present at the level of 10 fmol/μl in a mixture containing tryptic peptides from 5 proteins at the level of 2 pmol/μl. Aliquots corresponding to 0.5 μl of the above solutions (tryptic peptides from 1 pmol of each protein plus 5 fmol of phosphopeptide, DRVpYIHPF, SEQ ID NO: 1) were analyzed by mass spectrometry. (A) Selected ion chromatogram, SIC, or plot of the ion current vs. scan number for m/z 564.5 corresponding to the $(M+2H)^{++}$ of the phosphopeptide, DRVpYIHPF (SEQ ID NO: 1). (B) MS/MS spectrum characteristic of the sequence, DRVpYIHPF (SEQ ID NO: 1), recorded on ions of m/z 564.5 in scans 610–616. (C) Electrospray ionization mass spectrum recorded during this same time interval. Abundant ions from tryptic peptides non-specifically bound to the IMAC column obscure the signal at m/z 564.5 for DRVpYIHPF (SEQ ID NO: 1). (D) SIC for m/z 578.5 corresponding to the (M+2H)++ ion for the dimethyl ester of DRVpYIHPF (SEQ ID NO: 1). (E) MS/MS spectrum characteristic of the sequence, DRVpYIHPF (SEQ ID NO: 1), recorded in on ions of m/z 578.5 in scans 151–163. (F) Electrospray ionization mass spectrum recorded in scan 154 showing the parent ion, m/z 578.5 for the phosphopeptide dimethyl ester and the absence of signals for tryptic peptides non specifically bound to the IMAC column.

Figure 2:
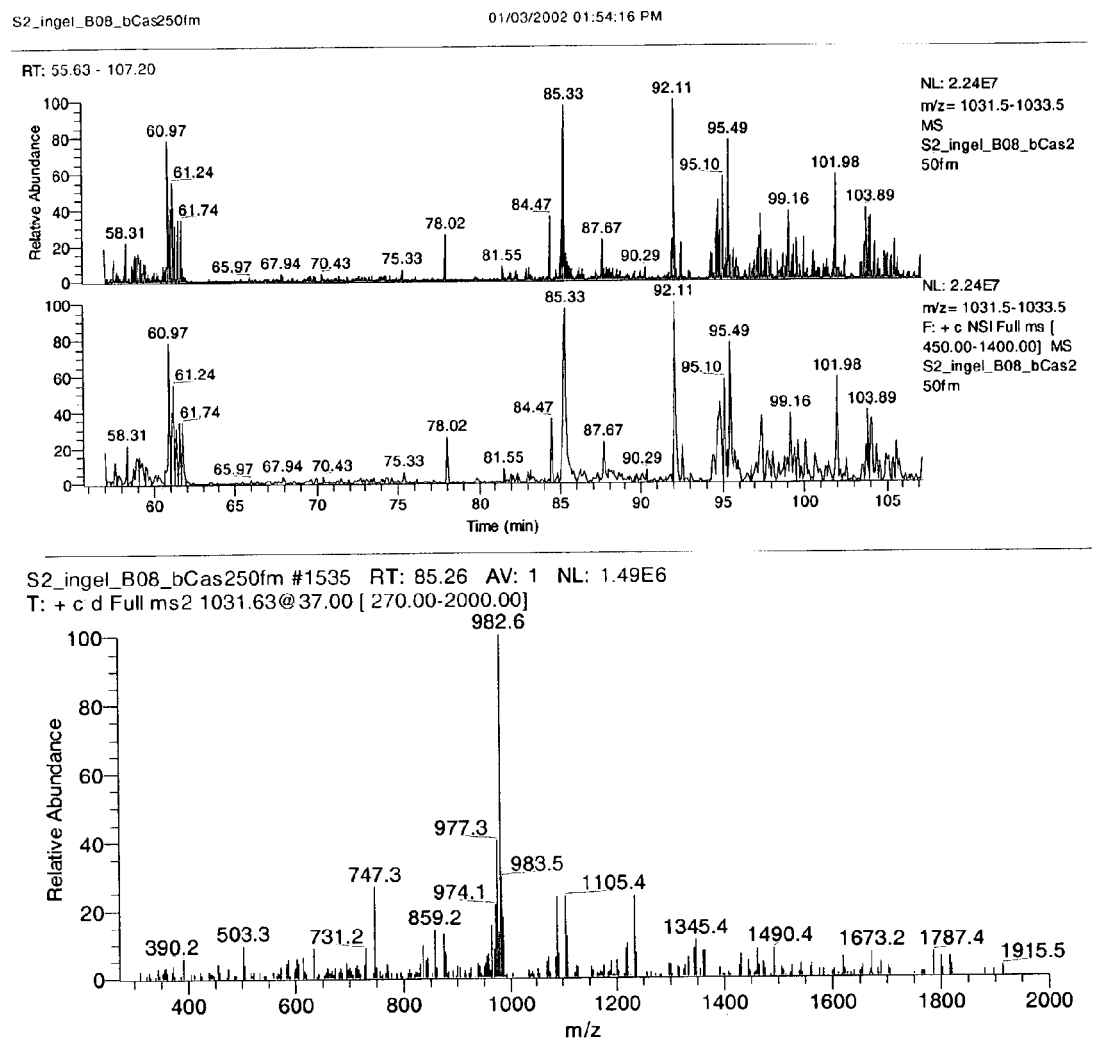

FIG. 2. Shows the result (top) of phosphopeptide β-casein analyzed by extracted ion chromatography from the HPLC separation, showing the β-casein peak at 30.71 min, and result (bottom) of the phosphopeptide β-casein analyzed by MS/MS scan at m/z=1031.5, showing individual peptide fragments of said phosphopeptide.

DETAILED DESCRIPTION OF THE INVENTION

The current progression from genomics to proteomics is fueled by the realization that many properties of proteins (e.g., interactions, post-translational modifications) cannot be predicted from a DNA sequence. The present invention provides a method useful to identify phosphorylated amino acid sites within peptide analytes. In certain preferred embodiments, the subject method is used to identify phosphate modified serine, threonine, tyrosine, histidine, arginine, lysine, cysteine, glutamic acid and aspartic acid residues, more preferably to identify phosphoserine-, phosphothreonine- and phosphotyrosine-containing peptides.

Unlike the prior art methods, which require conversion of the modified amino acid residue to another chemical entity which can be used to purify a particular peptide, the subject method is based on affinity capture by way of the originally modified amino acid residue following treatment of the pepticle with agents which modify other residues in the peptide which might otherwise interfere with the affinity capture process.

Phosphopeptides bind Fe(III) with high selectivity, so are amenable to affinity purification using Fe(III)-immobilized metal-ion affinity chromatography (IMAC) techniques. However, the presence of hydroxyl and carboxyl groups in sample peptides, e.g., due to a free carboxyl terminus or the presence of acidic side chains such as glutamic acid and aspartic acid, can reduce the efficiency of purification by contributing to non-specific binding to the metal column. Conversion of these side chains to neutral derivatives, such as by alkyl-esterification (which converts Glu and Asp to their neutral, alkyl ester derivatives, and also converts the C-terminal carboxyl group to an alkyl ester) or by treatment with diazomethane (Knapp, D. R., Methods in Enzymology, 193, 1990, p314–329) can be used to reduce such non-specific binding. Phosphate groups, if present, are not neutralized under the reaction conditions and are, accordingly, still available for coordinating the metal ion. Thus, the resulting peptide mixture is contacted with a metal affinity column or resin which retains only peptides which bear the phosphate groups. The other peptides "flow through" the column. The phosphopeptides can then be eluted in a second step and analyzed by mass spectrometry, such as LC/MS/MS. Sequencing of the peptides can reveal both their identity and the site of phosphorylation.

To further illustrate, alkyl esters of free carboxyl groups in a peptide can be formed by reaction with alkyl halides and salts of the carboxylic acids, in an amide-type solvent, particularly dimethylformamide, in the presence of an iodine compound. In other embodiments, the reaction can be carried out with equimolecular amounts of an alkyl halide and a tertiary aliphatic amine.

In yet another embodiment, the method of the present invention can include esterification of the free carboxylic groups by reacting a salt of the carboxylic acid with a halogenated derivative of an aliphatic hydrocarbon, a cycloaliphatic hydrocarbon or an aliphatic hydrocarbon bearing a cyclic substituent in an aqueous medium, and in the presence of a phase transfer catalyst. By the expression "phase transfer catalyst" is intended a catalyst which transfers the carboxylate anion from the aqueous phase into the organic phase. The preferred catalysts for the process of the invention are the onium salts and more particularly quaternary ammonium and/or phosphonium salts.

The alkyl ester of the dipeptide is most preferably a methyl ester and may also be an ethyl ester or alkyl of up to about four carbon atoms such as propyl, isopropyl, butyl or isobutyl.

In still other embodiments, the carboxyl groups can be modified using reagents which are traditionally employed as carboxyl protecting groups or cross-coupling agents, such as 1,3-dicyclohexylcarbodiimide (DCC), 1,1' carbonyldiimidazole (CDI), 1-ethyl-3-(3-dimethylaminopropyl) carbodiimide hydrochloride (EDC), benzotriazol-1-yl-oxytris(dimethylamino) phosphonium hexafluorophosphate (BOP), and 1,3-Diisopropylcarbodiimide (DICD).

In certain embodiments, the proteins or protein mixtures are further processed, e.g., cleaved chemically or enzymatically, to reduce to the proteins to smaller peptides fragments. In a preferred embodiment, treatment with an enzyme which produces a carboxy terminal lysine and/or arginine residue, such as trypsin, Arg-C and Lys-C, or a combination thereof, is employed. This digestion step may not be necessary if the proteins are relatively small.

In certain embodiments, the reactants and reaction conditions can be selected such that differential isotopic labeling can be carried out across multiple different samples to generate substantially chemically identical, but isotopically distinguishable, peptides. In this way, the source of particular samples can be encoded in the label. This technique can be used to quantitate differences in phosphorylation patterns and/or levels of phosphorylation between two or more samples. By way of illustration, the esterification reaction can be performed on one sample in the matter described above. In another sample, esterification is performed by deuterated or tritiated alkyl alcohols, e.g., $D_3COD$ ($D_4$ methyl-alcohol), leading to the incorporation of three deuterium atoms instead of hydrogen atoms for each site of esterification. Likewise, $^{18}O$ can be incorporated into peptides. The peptide mixtures from the two samples are then mixed and analyzed together, for example by LC/MS/MS. The phosphopeptides will be detected as light and heavy forms, and the relative ratio of peak intensities can be used to calculate the relative ratio of the phosphorylation in the two cases.

It can also be advantageous to perform one methylesterification reaction on the whole protein with methylalcohol for both samples. Subsequent to enzymatic digestion, one of the samples is then further esterified with D4 Methyl-alcohol. This leads to the incorporation of three deuterium atoms in each peptide rather than a variable number depending on the number of acidic residues in the peptide.

To complete the analysis, the sample may be further separated by reverse phase chromatography and on-line mass spectrometry analysis using both MS and MS/MS. To illustrate, the sequence of isolated peptides can be determined using tandem MS (MSn) techniques, and by application of sequence database searching techniques the protein from which the sequenced peptide originated can be identified. In general, at least one peptide sequence derived from a protein will be characteristic of that protein and be indicative of its presence in the mixture. Thus, the sequences of the peptides typically provide sufficient information to identify one or more proteins present in a mixture.

Quantitative relative amounts of proteins in one or more different samples containing protein mixtures (e.g., biological fluids, cell or tissue lysates, etc.) can be determined using isotopic labeling as described above. In this method, each sample to be compared is treated with a different isotopically labeled reagent. The treated samples are then combined, preferably in equal amounts, and the proteins in the combined sample are enzymatically digested, if necessary, to generate peptides. As described above, peptides are isolated by affinity purification and analyzed by MS. The relative amounts of a given protein in each sample is determined by comparing relative abundances of the ions generated from any differentially labeled peptides originating from that protein. More specifically, the method can be applied to screen for and identify proteins which exhibit differential levels of phosphorylation in cells, tissue or biological fluids.

The method of the present invention is useful for a variety of applications. For example, it permits the identification of enzyme substrates which are phosphorylated in response to different environmental cues provided to a cell. Identification of those substrates, in turn, can be used to understand the intracellular signaling pathways involved in any particular cellular response, as well as to identify the enzyme responsible for catalyzing the phosphorylation. To further illustrate, changes in phosphorylation states of substrate proteins can be used to identify kinases and/or phosphatases which are activated or inactivated in a manner dependent on particular cellular cues. In turn, those enzymes can be used as drug screening targets to find agents capable of altering their activity and, therefore, altering the response of the cell to particular environmental cues. So, for example, kinases and/or phosphatases which are activated in transformed (tumor) cells can be identified through their substrates, according to the subject method, and then used to develop anti-proliferative agents which are cytostatic or cytotoxic to the tumor cell.

In other embodiments, the present method can be used to identify a treatment which can modulate the phosphorylation of an amino acid in a target protein without any knowledge of the upstream enzymes which produce the modified target protein. By comparing the level of phosphorylation before and after certain treatments, one can identify the specific treatment which leads to a desired change in the level of phosphorylation of one or more target proteins. To illustrate, one can screen a library of compounds, for example, small chemical compounds from a library, for their ability to induce or inhibit phosphorylation of a target polypeptide. In other instances, it may be desirable to screen compounds for their ability to induce or inhibit the dephosphorylation of a target polypeptide (i.e., by a phosphatase).

Similar treatments are not limited to small chemical compounds. For example, a large number of known growth factors, cytokines, hormones and any other known agents known to be capable of being phosphorylated are also within the scope of the invention.

In addition, treatments are not limited to chemicals. Many other environmental stimuli are also known to be able to cause phosphorylation. For example, osmotic shock may activate the p38 subfamily of MAPK (Mitogen Activated Protein Kinase) and induce the phosphorylation of a number of downstream targets. Stress, such as heat shock or cold shock, may activate the JNK/SAPK (Jun N-terminal Kinase/Stress-Activated Protein Kinase) subfamily of MAPK and induce the phosphorylation of a number of downstream targets. Other treatments such as pH change may also stimulate signaling pathways characterized by the post-translational modification of key signaling components.

To illustrate, one may wish to identify the effect of treating cells with a growth factor. More specifically, one may desire to identify the specific signal transduction pathways involved downstream of a growth factor. By comparing phosphorylation levels of certain candidate polypeptides before and after the growth factor treatment, one can use the method of the instant invention to determine precisely which downstream signaling pathways of interest are activated or down regulated. This, in turn, also leads to the identification of potential drug screening targets if such signaling pathways are to be modulated.

In connection with such methods, the instant invention also provides a method for conducting a drug discovery business, comprising: i) by suitable methods mentioned above, determining the identity of a compound which modulates phosphorylation of an amino acid in a target polypeptide; ii) conducting therapeutic profiling of the compound identified in step i), or further analogs thereof, for efficacy and toxicity in animals; and, iii) formulating a pharmaceutical preparation including one or more compounds identified in step ii) as having an acceptable therapeutic profile. Such business method can be further extended by including an additional step of establishing a distribution system for distributing the pharmaceutical preparation for sale, and may optionally include establishing a sales group for marketing the pharmaceutical preparation.

The instant invention also provides a business method comprising: i) by suitable methods mentioned above, determining the identity of a compound which modulates phosphorylation of an amino acid in a target polypeptide; ii) licensing, to a third party, the rights for further drug development of compounds which alter the level of modification of the target polypeptide.

The instant invention also provides a business method comprising: i) by suitable methods mentioned above, determining the identity of the polypeptide and the nature of the phosphorylation induced by the treatment; ii) licensing, to a third party, the rights for further drug development of compounds which alter the level of phosphorylation of the polypeptide.

EXAMPLE

Phosphoproteome Analysis by Mass Spectrometry

Following the methodology of the present invention, it is now possible to characterize most, if not all, phosphoproteins from a whole cell lysate in a single experiment. Proteins were digested with trypsin and the resulting peptides then converted to methyl esters, enriched for phosphopeptides by immobilized metal affinity chromatography (IMAC) and analyzed by nanoflow HPLC/electrospray ionization mass spectrometry.

In an initial experiment, B-casein was digested with trypsin and analyzed using the method of the invention. Results of this experiment are shown in FIG. 2.

More than a 1,000 phosphopeptides were detected when the methodology was applied to the analysis of a whole cell lysate from S. cerevisiae. Sequences, including 383 sites of phosphorylation derived from 216 peptides, were determined. Of these, 60 were singly phosphorylated, 145 doubly phosphorylated, and 11 triply phosphorylated. To validate the approach, these results were compared with the literature, revealing 18 previously identified sites, including the doubly phosphorylated motif pTXpY derived from the activation loop of two MAP kinases. We note that the methodology can easily be extended to display and quantitate differential expression of phosphoproteins in two different cell systems, and therefore demonstrates an approach for "phosphoprofiling" as a measure of cellular state.

We prepared a standard mixture of tryptic peptides containing a single phosphopeptide and then analyzed the mixture before and after converting the peptides to the corresponding methyl esters. This rendered the IMAC selective for phosphopeptides and eliminated confounding binding through carboxylate groups. Equimolar quantities of glyceraldehyde 3-phosphate dehydrogenase, bovine serum albumin, carbonic anhydrase, ubiquitin, and β-lactoglobulin were digested with trypsin (approximately 125 predicted cleavage sites) and then combined with the phosphopeptide DRVpYIHPF (SEQ ID NO: 1, lower case p precedes a phosphorylated residue), to give a mixture which contained tryptic peptides at the 2 pmol/μl level and phosphopeptide at the 10 fmol/μl level. All experiments were performed on 0.5 μl aliquots of this solution.

Shown in FIG. 1 are the results obtained when a 0.5 μl aliquot of the standard mixture was analyzed by a combination of IMAC[5,6] and nanoflow-HPLC on an LCQ ion-trap mass spectrometer. In this experiment, the instrument was set to cycle between two different scan functions every 2 sec throughout the HPLC gradient. Electrospray ionization spectra were recorded in the first of the two scans. MS/MS spectra on the $(M+2H)^{++}$ ion of the phosphopeptide, DRVpYIHPF (SEQ ID NO: 1, m/z 564.5) were recorded in the second scan of the cycle. FIG. 1A shows a selected-ion-chromatogram (SIC) or plot of the ion current observed for m/z 564.5 as a function of scan number. Note that a signal at this m/z value is observed at numerous points in the chromatogram. Only ions at m/z 564.5 in scans 610–616 fragment to generate MS/MS (tandem Mass Spectrometry) spectra characteristic of the phosphopeptide, DRVpYIHPF (SEQ ID NO: 1, FIG. 1B). We conclude that DRVpYIHPF (SEQ ID NO: 1) elutes from the HPLC column in scans 610–616.

Shown in FIG. 1C is an electrospray ionization mass spectrum recorded during this same time period. Note that the spectrum contains signals of high intensity (ion currents of $1-3 \times 10^9$) corresponding to non-phosphorylated tryptic peptides in the mixture but no signal above the chemical noise level for the phosphopeptide (m/z 564.5). We conclude that tryptic peptides containing multiple carboxylic acid groups can bind efficiently to the IMAC column, elute during the HPLC gradient, and suppress the signal from trace level phosphopeptides in the mixture.

To prevent binding of non-phosphorylated peptides to the IMAC column, all peptides in the standard mixture were converted to the corresponding peptide methyl esters and a 0.5 μl aliquot was then analyzed by the protocol outlined above. To detect the phosphopeptide in which both carboxylic acid groups had been esterified, MS/MS spectra were recorded on the $(M+2H)^{++}$ ion at m/z 578.5. The SIC for m/z 578.5 (FIG. 1D) suggests that the phosphopeptide dimethyl ester elutes during scans 151–163. Indeed, MS/MS spectra (FIG. 1E) recorded in this time window all contain the predicted fragments expected for the dimethyl ester of DRVpYIHPF (SEQ ID NO: 1). FIG. 1F shows an electrospray ionization mass spectrum recorded in the same area of the chromatogram (scan #154). Note that the parent ion, m/z 578.5, for the phosphopeptide dimethyl ester is now observed with a signal/noise of 3/1 and an ion current of $2 \times 10^7$. This signal level on the LCQ is not a typical for phosphopeptide samples at the 3–5 fmol level. Note also that signals above the chemical noise (ion current of $1 \times 10^7$) for non-phosphorylated tryptic peptides no longer appear in this electrospray ionization spectrum or in any other spectrum recorded throughout the entire chromatogram. We conclude that conversion of carboxylic acid groups to methyl esters reduces nonspecific binding by at least two orders of magnitude and allows detection of phosphopeptides in complex mixtures down to the level of at least 5 fmol with the LCQ instrument.

To further evaluate the above protocol, we next analyzed a protein pellet (500 μg) obtained from a whole cell lysate of S. cerevisiae. If the average mol. wt. (molecular weight) of yeast proteins is 25 kDa (kilo Dalton) and half the genome is expressed and isolated in the pellet, then the average quantity each protein in the sample is expected to be approximately 5 pmol. If one makes the further assumption that 30% of expressed proteins contain at least one covalently bound phosphate, the total number of phosphoproteins in the sample could easily exceed 1,000. To evaluate this possibility the pellet was digested with trypsin and the resulting peptides converted to peptide methyl esters. One-fifth of the resulting mixture was then fractionated by IMAC and analyzed by nano-flow HPLC on the LCQ ion trap mass spectrometer. Spectra were acquired with the instrument operating in the data-dependent mode throughout the HPLC gradient. Every 12–15 seconds the instrument cycled through acquisition of a full scan mass spectrum and 5 MS/MS spectra recorded sequentially on the 5 most abundant ions present in the initial MS scan. More than 1,500 MS/MS spectra were recorded in this mode of operation during the chromatographic separation.

Data acquired in the above experiment was analyzed both by a computer algorithm, the Neutral Loss Tool, and also by SEQUEST. The Neutral Loss Tool searches MS/MS spectra for fragment ions formed by loss of phosphoric acid, 32.6, 49 or 98 Da from the $(M+3H)^{+++}$, $(M+2H)^{++}$ and $(M+H)^+$ ions, respectively. Phosphoserine and phosphothreonine, but not phosphotyrosine, lose phosphoric acid readily during the collision activation dissociation process in the ion trap mass spectrometer. Thus, appearance of fragment ions 32.6, 49 or 98 Da below the triply, doubly or singly charged precursor ions in peptide MS/MS spectra strongly suggests that the peptide contains at least one phosphoserine or phosphothreonine residue. In the above experiment, more than 1,000 different phosphoserine or phosphothreonine containing peptides were detected in the yeast whole cell lysate with the Neutral Loss Tool.

To identify phosphopeptides in the above sample, MS/MS spectra were searched with the SEQUEST algorithm against yeast protein database (obtained from the Saccharomyces Genome Database (SGD) genome-www.stanford.edu/Saccharomyces/). Of the 216 sequences confirmed, 60 (28%) were singly phosphorylated, 145 (67%) were doubly phosphorylated, and 11 (5%) were triply phosphorylated.

This clearly indicates the potential of the phosphoprofiling approach as a measure of cellular activation states. In fact, we identified 171 different proteins, including abundant species such as the heat shock proteins as well as those involved in carbohydrate metabolism and protein synthesis. Rare proteins, such as the cell cycle regulatory molecules and cytoplasmic proteins, were also observed. Of the 216 confirmed peptide sequences, 66 have sequences which correspond to a codon bias of less than 0.1 and are therefore likely to be expressed in low copy number.

Eighty-five additional phosphopeptides were identified by recording MS/MS on the sample eluted from the IMAC column after it had been treated with alkaline phosphatase to remove covalently bound phosphate. In this experiment, peptide methyl esters were eluted from the IMAC column directly to a second column packed with F7m Polyvinyl spheres containing immobilized alkaline phosphatase. Dephosphorylated peptides were then eluted to a standard nano-flow HPLC column and analyzed on an LCQ instrument using the data dependent scan protocol described above. This approach has the advantage that the resulting MS/MS spectra usually contain a larger number of abundant, sequence-dependent, fragment ions than those recorded on the corresponding phosphorylated analogs. This, in turn, improves the likelihood that the SEQUEST algorithm will find a unique match in the protein database. The disadvantage of the protocol is that the resulting MS/MS spectra no longer contain information on the number and location of the phosphorylated residues within the peptide.

Finally, we note that the above methodology can be modified easily to allow quantitation and/or differential display of phosphoproteins expressed in two different samples. For this experiment, peptides are converted to methyl esters from one sample with do-methanol and from the other sample with $d_3$-methanol. The two samples are combined, fractionated by IMAC, and the resulting mixture of labeled and unlabeled phosphopeptides is then analyzed by nanoflow HPLC/electrospray ionization on a newly constructed Fourier transform mass spectrometer. This instrument operates with a detection limit in the low attomole level. Signals for peptides present in both samples appear as doublets separated by n(3Da)/z (where n=the number of carboxylic acid groups in the peptide and z=the charge on the peptide). The ratio of the two signals in the doublet changes as a function of the expression level of the particular phosphoprotein in each sample. Peptides of interest are then targeted for sequence analysis in a subsequent analysis performed on the ion trap instrument as discussed above.

Fractionation of peptides on these columns is based upon their affinity for $Fe^{+3}$ which is coordinated to chelating agents covalently attached to the packing material.

Protein extraction from S. cerevisiae. Yeast strain 2124 MATa ade2-1, ade6-1, leu2-3, 112, ura3-52, his3Δ1, trpl-289, can1cyh2 bar1::KAN (40 ml) was grown in YPD at 23° C. to a density of $1 \times 10^7$ cells/ml. The cell pellet was re-suspended in 1.5 ml of Trizol (Gibco-BRL) and cell lysis performed by homogenization with glass beads in 3 consecutive sessions of 45 sec each in a Fastprep FP120 shaker (Savant). Total yeast protein, free of nucleic acids, was extracted from this yeast lysate using Trizol according to the manufacturer's directions (Gibco-BRL). The protein pellet was re-suspended in 1% SDS (Sodium Dodecyl Sulfate) and dialyzed against 1% SDS using a Slyde-A-Lyzer, 10,000 MW (Molecular Weight) cutoff (Pierce), to remove small molecules and stored at −80° C. To follow the removal of nucleotides, 0.1 μl of a $P^{32}$ CTP (Amersham-Pharmacia) was added to a 10 ml equivalent of lysed cells. Aliquots were removed after each step in the purification and the amount of nucleotide quantitated by Scintillation with Scintisafe EconoF (Fischer). Yeast protein, 500 μg (approximately 10 nmol), in 500 μl of 100 mM animonium acetate (pH 8.9), was digested with trypsin (20 μg)(Promega) overnight at 37° C. Solvent was removed by lyophilization and the residue reconstituted in 400 μl of 2N methanolic HCl and allowed to stand at room temperature for 2 h. Solvent was lyophilized and the resulting peptide methyl esters were dissolved in 120 μl of a solution containing equal parts of methanol, water and acetonitrile. An aliquot corresponding to 20% of this material (2 nmol of yeast protein) was subjected to chromatography and mass spectrometry as described below.

Chromatography. Construction of immobilized metal affinity chromatography (IMAC) columns has been described previously[9]. Briefly, 360 μm O.D. (Optical Density)×100 μm I.D. (Inner Diameter) fused silica (Polymicro Technologies, Phoenix, Ariz.) was packed with 8 cm POROS 20 MC (PerSeptive Biosystems, Framingham, Mass.). Columns were activated with 200 μl 100 mM FeCl$_3$ (Aldrich, Milwaukee, Wis.) and loaded with either 0.5 μl of the above standard mixture or sample corresponding to peptides derived from 100 μg (10 nmol) of protein extract from S. cerevisiae. To remove non-specific binding peptides, the column was washed with a solution containing 100 mM NaCl (Aldrich) in acetonitrile (Mallinkrodt, Paris, Ky.), water, and glacial acetic acid (Aldrich) (25:74:1, v/v/v). For sample analysis by mass spectrometry, the affinity column was connected to a fused silica pre-column (6 cm of 360 μm O.D.×100 μm I.D.) packed with 5–20 μm C18 particles (YMC, Wilmington, N.C.). All column connections were made with 1 cm of 0.012" I.D.×0.060" O.D. Teflon tubing (Zeus, Orangeburg, S.C.). Phosphopeptides were eluted to the pre-column with 10 μl 50 mM Na$_2$HPO$_4$ (Aldrich) (pH 9.0) and the pre-column was then rinsed with several column volumes of 0.1% acetic acid to remove Na$_2$HPO$_4$. The pre-column was connected to the analytical HPLC column (360 μm O.D.×100 μm I.D. fused silica) packed with 6–8 cm of 5 μm C18 particles (YMC, Wilmington, N.C.). One end of this column contained an integrated laser pulled ESI (ElectroSpray Ionization) emitter tip (2–4 μm in diameter)[14]. Sample elution from the HPLC column to the mass spectrometer was accomplished with a gradient consisting of 0.1% acetic acid and acetonitrile. For removal of phosphate from the tryptic peptides, the IMAC column was connected to a fritted 360 μm O.D.×200 μm I.D. fused silica capillary packed with F7m (Polyvinyl spheres), containing immobilized alkaline phosphatase (MoBiTech, Marco Island, Fla.). Phosphopeptides were eluted from the IMAC column through the phosphatase column onto a pre-column with 25 μL of 1 mM ethylenediaminetetraacetic acid (EDTA) (pH in the range of from about 5.0 to about 9.0), and the pre-column was then rinsed with several column volumes of 0.1% acetic acid to remove EDTA. Alternatively, phosphopeptides can be eluted using ascorbic acid. The pre-colunm was connected to an analytical HPLC column. Sample elution from the HPLC column to the mass spectrometer was accomplished with a gradient consisting of 0.1% acetic acid and acetonitrile.

Mass Spectrometry. All samples were analyzed by nano-flow-HPLC/microelectrospray ionization on a Finnigan LCQ ion trap (San Jose, Calif.). A gradient consisting of 0–40% B in 60 min, 40–100% B in 5 min (A=100 mM acetic acid in water, B=70% acetonitrile, 100 mM acetic acid in water) flowing at approximately 10 nL/min was used to elute peptides from the reverse-phase column to the mass spectrometer through an integrated electrospray emitter tip[14]. Spectra were acquired with the instrument operating in the data-dependent mode throughout the HPLC gradient. Every 12–15 sec, the instrument cycled through acquisition of a full scan mass spectrum and 5 MS/MS spectra (3 Da window; precursor m/z+/−1.5 Da, collision energy set to 40%, dynamic exclusion time of 1 minute) recorded sequentially on the 5 most abundant ions present in the initial MS scan. To perform targeted analysis of the phosphopeptide in the standard mixture, the ion trap mass spectrometer was set to repeat a cycle consisting of a full MS scan followed by an MS/MS scan (collision energy set to 40%) on the (M+2H)$^{++}$ of DRVpYIHPF (SEQ ID NO: 1) or its methyl ester (m/z 564.5 and 578.5, respectively). The gradient employed for this experiment was 0–100% B in 30 minutes for the un-derivatized sample, 0–100% B in 17 minutes for derivatized sample (A=100 mM acetic acid in water, B=70% acetonitrile, 100 mM acetic acid in water).

Database Analysis. All MS/MS spectra recorded on tryptic phosphopeptides derived from the yeast protein extract were searched against the S. cerevisiae protein database by using the SEQUEST algorithm[10]. Search parameters included a differential modification of +80 Da (presence or absence of phosphate) on serine, threonine and tyrosine and a static modification of +14 Da (methyl groups) on aspartic acid, glutamic acid, and the C-terminus of each peptide.

REFERENCES

1. Hubbard, M. J. and Cohen, P. On target with a new mechanism for the regulation of protein phosphorylation. *Trends Biochem. Sci.* 18, 172–177 (1993).
2. Annan, R., Huddleston, M., Verma, R., Deshaies, R. & Carr, S. A Multidimensional Electrospray MS-Based Approach to Phosphopeptide Mapping. *Anal. Chem.* 73, 393–404 (2001).
3. Oda, Y., Nagasu, T. & Chait, B. Enrichment analysis of phosphorylated proteins as a tool for probing the phosphoproteome. *Nat. Biotechnol.* 19, 379–382 (2001).
4. Zhou, H., Watts, J. & Aebersold, R. A systematic approach to the analysis of protein phosphorylation. *Nat. Biotechnol.* 19, 375–378 (2001).
5. Andersson, L. and Porath, J. Isolation of phosphoproteins by immobilized metal (Fe3+) affinity chromatography. *Anal. Biochem.* 154, 250–254 (1986b)
6. Michel, H., Hunt, D. F., Shabanowitz, J. and Bennett, J. Tandem mass spectrometry reveals that three photosystem II proteins of spinach chloroplasts contain N-acetyl-O-phosphothreonine at their NH$_2$ termini. *J. Biol. Chem.* 263, 1123–1130 (1988).
7. Muszynska, G., Dobrowolska, G., Medin, A., Ekman, P. & Porath, J. O. Model studies on iron(III) ion affinity chromatography. II. Interaction of immobilized iron(III) ions with phosphorylated amino acids, peptides and proteins. *J. Chrom.* 604, 19–28 (1992).
8. Nuwaysir, L. & Stults, J. Electrospray ionization mass spectrometry of phosphopeptides isolated by on-line immobilized metal-ion affinity chromatography. *J. Amer. Soc. Mass Spectrom.* 4, 662–669 (1993).
9. Zarling, A. L. et al. Phosphorylated peptides are naturally processed and presented by major histocompatibility complex class I molecules in vivo. *J. Exp. Med.* 192, 1755–1762 (2000).
10 Eng, J., McCormack, A. L. and Yates, J. R. An approach to correlate tandem mass spectral data of peptides with amino acid sequences in a protein database. *J. Amer. Soc. Mass Spectrom*, 5, 976–989 (1994).
11. Bennetzen, J. L. & Hall, B. D. Codon selection in yeast. *J Biol Chem* 257, 3026–3031 (1982).
12. Zhang, X. et al. Identification of phosphorylation sites in proteins separated by polyacrylamide gel electrophoresis. *Anal Chem* 70, 2050–2059 (1998).
13. Amankwa, L. N., Harder, K., Jirik, F. & Aebersold, R. High-sensitivity determination of tyrosine-phosphorylated peptides by on-line enzyme reactor and electrospray ionization mass spectrometry. *Prot. Sci.* 4, 113–125 (1995).
14. Martin, S. E., Shabanowitz, J., Hunt, D. F. & Marto, J. A. Subfemtomole ms and ms/ms peptide sequence analysis using nano-hplc micro-esi fourier transform ion cyclotron resonance mass spectrometry. *Anal Chem* 72, 4266–4274 (2000).

We claim:
1. A method for identifying phosphorylated proteins in a protein-containing sample, comprising:
   (i) providing one or more protein-containing samples and an affinity capture reagent for isolating, from said samples, those proteins which have been phosphorylated, wherein the affinity capture reagent captures the phosphorylated proteins;

(ii) processing said samples to chemically modify at least one of the C-terminal carboxyl group and amino acid side chains of proteins in said samples wherein said chemical modification is carried out at glutamic acid and aspartic acid residues to generate neutral products at said residues;

(iii) isolating the phosphorylated proteins from said samples by capturing them with the affinity capture reagent; and, (iv) determining the identity of the isolated proteins by mass spectroscopy.

2. The method of claim 1, wherein the proteins are further cleaved into smaller peptide fragments before, after or during the step of processing the protein samples.

3. The method of claim 2, wherein the identity of the isolated proteins are determined by obtaining amino acid sequence mass spectra for the isolated proteins or peptide fragments thereof, and searching one or more sequence databases for the sequence observed for the isolated proteins or peptide fragments thereof.

4. The method of claim 2, carried out on multiple different protein samples, wherein the proteins or fragments thereof of each protein samples are isotopically labeled in a manner which permits discrimination of mass spectroscopy data between protein samples.

5. The method of claim 2, wherein the proteins are cleaved by enzymatic hydrolysis to produce peptide fragments having carboxy-terminal lysine or arginine residues.

6. The method of claim 5, wherein the proteins are cleaved by treatment with trypsin.

7. The method of claim 1, wherein the proteins are mass-modified with isotopic labels before, after or during the step of processing the protein samples.

8. The method of claim 1, wherein the isolated proteins are further separated by reverse phase chromatography before analysis by mass spectroscopy.

9. The method of claim 1, wherein the isolated proteins are identified from analysis using tandem mass spectroscopy techniques.

10. The method of claim 9, wherein the identity of the isolated proteins are determined by obtaining amino acid sequence mass spectra for the isolated proteins, and searching one or more sequence databases for the sequence observed for the isolated proteins.

11. The method of claim 2, wherein the identity of the isolated proteins are determined by searching molecular weight databases for the molecular weight observed by mass spectroscopy for an isolated protein or peptide fragment thereof.

12. The method of claim 1, wherein the identity of the isolated proteins axe determined by obtaining amino acid sequence mass spectra for the isolated proteins, and searching one or more sequence databases for the sequence observed for the isolated proteins.

13. The method of claim 1, wherein the affinity capture reagent is an immobilized metal affinity chromatography medium.

14. The method of claim 1, wherein the side chains of glutamic acid and aspartic acid residues are modified by alkyl-esterification.

15. The method of claim 1, wherein the protein sample is a mixture of different proteins.

16. The method of claim 15, wherein the protein sample is derived from a biological fluid, or a cell or tissue lysates.

17. The method of claim 1, carried out on multiple different protein samples, wherein the proteins of each protein samples are isotopically labeled in a manner which permits discrimination of mass spectroscopy data between protein samples.

18. A method for identifying phosphorylated peptides in a peptide-containing sample, comprising:

(i) providing one or more peptide-containing samples and an affinity capture reagent for isolating, from the samples, those peptides which have been phosphorylated, wherein the affinity capture reagent captures the phosphorylated peptides;

(ii) processing said samples to chemically modify at least one of the C-terminal carboxyl group and amino acid side chains of peptides in said samples wherein said chemical modification is carried out at glutamic acid and aspartic acid residues to generate neutral products at said residues;

(iii) isolating the phosphorylated peptides from said samples by capturing them with the affinity capture reagent; and, (iv) determining the identity of the isolated peptides by mass spectroscopy.

* * * * *

UNITED STATES PATENT AND TRADEMARK OFFICE
CERTIFICATE OF CORRECTION

| | | |
|---|---|---|
| PATENT NO. | : 7,026,167 B2 | |
| APPLICATION NO. | : 10/330888 | |
| DATED | : April 11, 2006 | |
| INVENTOR(S) | : Donald F. Hunt, Forest M. White and Scott Ficarro | |

It is certified that error appears in the above-identified patent and that said Letters Patent is hereby corrected as shown below:

At Column 1, Line 11, the following paragraph is inserted immediately after the first paragraph:

--STATEMENT REGARDING FEDERALLY SPONSORED RESEARCH OR DEVELOPMENT

This invention was made with government support under Grant No. GM37537 awarded by the National Institutes of Health. The government has certain rights in the invention.--

Signed and Sealed this

Twentieth Day of April, 2010

David J. Kappos
*Director of the United States Patent and Trademark Office*